United States Patent [19]

Pollock et al.

[11] 4,402,697

[45] Sep. 6, 1983

[54] METHOD FOR INHIBITING MINERALIZATION OF NATURAL TISSUE DURING IMPLANTATION

[75] Inventors: Elisabeth M. Pollock, Sandy; David J. Lentz, Salt Lake City, both of Utah

[73] Assignee: Extracorporeal Medical Specialties, Inc., King of Prussia, Pa.

[21] Appl. No.: 411,191

[22] Filed: Aug. 25, 1982

[51] Int. Cl.³ .............................................. A61F 1/22
[52] U.S. Cl. ................................ 8/94.11; 3/1; 3/1.4; 3/1.5
[58] Field of Search ......................................... 8/94.11

[56] References Cited

U.S. PATENT DOCUMENTS

| | | | |
|---|---|---|---|
| 3,966,401 | 6/1976 | Hancock et al. | 8/94.11 |
| 4,050,893 | 9/1977 | Hancock et al. | 8/94.11 |
| 4,323,358 | 4/1982 | Lentz et al. | 8/94.11 |

*Primary Examiner*—Maria Parrish Tungol
*Attorney, Agent, or Firm*—Lawrence D. Schuler

[57] ABSTRACT

Natural tissues fixed with a tanning solution such as glutaraldehyde and intended for implantation in humans, e.g., porcine heart valve prosthetic devices, are treated with a solution of a water soluble phosphate ester such as sodium dodecyl hydrogen phosphate to inhibit mineralization, particularly calcification, of the tissue after implantation.

26 Claims, No Drawings

METHOD FOR INHIBITING MINERALIZATION OF NATURAL TISSUE DURING IMPLANTATION

BACKGROUND OF INVENTION

This invention relates to the preparation of natural tissue for implantation, and more particularly, to the treatment of fixed tissue to inhibit mineralization, particularly calcification, upon implantation.

Animal tissues have in recent years found wide acceptance in the preparation of various prosthetic devices for use in humans. Most notable of these is the use of porcine heart valves to replace defective mitral, tricuspid and aortic valves in humans. Also of interest is the preparation of arteries, veins and human umbilical cords for use as arterial grafts and other tubular duct replacement in humans.

Porcine heart valves have been in use for several years with generally good results. The preparation of such valves for implantation is described in the literature and in the patent art as, for example, in U.S. Pat. Nos. 3,966,401 and 4,050,893. Briefly, the valve is excised from the donor heart, trimmed and cleaned, and fixed by immersion in a tanning fluid such as a 0.2% glutaraldehyde solution. After several hours of treatment, the fixed valve is removed from the glutaraldehyde, rinsed, mounted on a stent, and stored in a glutaraldehyde solution until ready for use.

One problem which has been associated with the porcine heart valve in some individuals is calcification of the valve leaflets after an extended period of time resulting in reduced flexibility and eventual loss of efficiency in the operation of the valve. Significant calcification is readily visible in an X-ray of the affected valve.

U.S. Pat. No. 4,323,358 discloses a method for inhibiting mineralization particularly calcification, of fixed natural tissue by treatment with a salt of a sulfated higher aliphatic alcohol such as sodium dodecyl sulfate.

It is an object of the present invention to provide another method to inhibit mineralization, and particularly calcification, of fixed natural tissue upon implantation.

It is a further object of this invention to provide a method for treatment of fixed porcine heart valve tissue to inhibit mineralization when used as a prosthetic valve replacement in humans.

These and other objects of the present invention will be apparent from the ensuing description and claims.

As used herein, the term "fixed" or "fixed tissue" refers to tissue which has been treated with a tanning solution such as 4% formaldehyde or 0.2% glutaraldehyde for a period of time and under conditions conventionally used to prepare natural tissue for implantation. The tanning process does not form any part of the present invention.

SUMMARY OF INVENTION

Natural tissue such as porcine heart valves which have been fixed for implantation in accordance with conventional procedures are treated prior to implantation with a solution of a water soluble phosphate ester having the formula

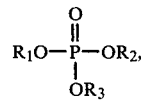

wherein at least one of $R_1$, $R_2$ and $R_3$ is an alkyl group containing from 7 to 15 carbon atoms. An example of a water soluble phosphate ester which may be used in the practice of the invention is sodium dodecyl hydrogen phosphate (SDHP).

The treatment may be effected in a 1% solution of SDHP in distilled water or an aqueous electrolyte solution at ambient temperatures and for a period of 7 days. The treated tissue is removed from the SDHP solution, rinsed, and returned to storage in sterile glutaraldehyde until needed for implantation.

DESCRIPTION OF PREFERRED EMBODIMENTS

In the method of the present invention, fixed natural tissue is treated with an aqueous solution of a water soluble phosphate ester having the formula

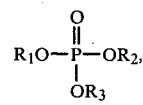

wherein at least one of $R_1$, $R_2$ and $R_3$ is an alkyl group containing from 7 to 15 carbons. In the preferred water soluble phosphate esters, $R_1$ is an alkyl group containing 7 to 15 carbons, $R_2$ is hydrogen and $R_3$ is selected from the group consisting of sodium, potassium, ammonium and organic amine. The preferred water soluble phosphate esters include the water soluble salts of monodecyl hydrogen phosphate, monododecyl hydrogen phosphate and monomyristyl hydrogen phosphate. Most preferably, the water soluble phosphate ester is sodium dodecyl hydrogen phosphate (SDHP); that is, in the most preferred water soluble phosphate ester, $R_1$ is a 12-carbon alkyl group, $R_2$ is hydrogen and $R_3$ is sodium. The alkyl unit may be straight chain or branched and mixtures of two or more phosphate esters may be used if the mixture is soluble in aqueous solution. The phosphate ester is preferably soluble in water at room temperature to a concentration of a least 2%, and preferably at least about 5%, by weight. In the preferred embodiment, the phosphate ester is dissolved in an aqueous electrolyte solution comprising up to about 1% by weight of sodium chloride, up to about 0.05% by weight each of potassium chloride, magnesium sulfate heptahydrate and dipotassium hydrogen phosphate, and up to about 0.1% by weight of sodium dihydrogen phosphate. As indicated above, sodium dodecyl hydrogen phosphate (SDHP) is most particularly preferred and its use is illustrated in the following detailed example. The formula of SDHP is

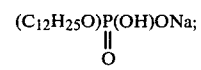

its molecular weight is 288.3.

An SDHP treatment solution (1% w/v) was prepared by dissolving 10 g. of SDHP in a sufficient quantity of an aqueous electrolyte solution (AES) to bring the total volume of treatment solution to 1 liter. Aqueous electrolyte solution (AES) is an aqueous solution containing approximately 0.8% by weight of sodium chloride, 0.04% by weight of potassium chloride, 0.02% by weight of magnesium sulfate heptahydrate, 0.02% by weight of dipotassium hydrogen phosphate and 0.08% sodium dihydrogen phosphate. The pH of the AES is adjusted to 7.35–7.45 with either 2 N sodium hydroxide or 2 N hydrochloric acid prior to use. The pH of the SDHP treatment solution was 3.0.

Fifty pieces of fixed porcine valve cusp tissue weighing from about 20 to 30 mg. each were rinsed in AES to remove the glutaraldehyde, then placed in 50 ml. of the SDHP treatment solution at an ambient temperature of 20°–25° C. for 7 days.

After completion of the SDHP treatment, the tissue pieces were rinsed in 0.2% glutaraldehyde solution and stored in 0.2% glutaraldehyde solution. Subsequently, the tissue pieces were sterilized for 24 hours in an aqueous solution containing 1% glutaraldehyde and 20% isopropyl alcohol, and stored in sterile 0.2% glutaraldehyde solution to await implantation.

The effectiveness of the SDHP treatment in retarding calcification of the fixed tissue was determined by animal implant studies according to the following procedure.

Male Sprague-Dawley rats weighing 180–200 g. were anesthetized and prepared for abdominal surgery under sterile conditions. The abdominal area was shaved and disinfected, and a lengthwise midline skin incision approximately 4 cm. long was made in the ventral surface. The skin was separated from the underlying muscle, and three small pouches were formed in the muscle on either side of the midline incision by a small incision followed by blunt dissection of the abdominal muscle wall. One piece of SDHP-treated tissue, rinsed in sterile saline to remove the glutaraldehyde, was inserted in each muscle pouch.

The skin incision was closed and the animal returned to its cage. Implantations were made in 5 rats for a total of 30 pieces of SDHP-treated tissue. A control group of 5 rats were implanted under identical conditions with a total of 30 pieces of fixed porcine valve cusp tissue not subjected to the SDHP treatment.

The rats from both the control group and the SDHP test group were sacrificed after twelve weeks and the implanted tissue examined for calcification by X-ray and by analysis for $Ca^{+2}$ levels. The entire abdominal muscle with implants in situ was excised and X-rayed. The implanted specimens were then removed and two set aside for histological examination. The remaining four implants were dissected free of surrounding tissue and extracted individually in 5 ml. of 0.6 N HCl at 70° C. for 96 hours. The extract solution was then assayed for calcium ion by atomic absorption spectrophotometry. Prior experience had established that, where tissue is analyzed and found to contain $Ca^{+2}$ levels of less than 1 μg. per mg. of wet tissue, all of the $Ca^{+2}$ so found is attributable to normal physiological processes and none is attributable to a process of mineralization. In other words, it can be concluded that no mineralization has occurred in tissue whose $Ca^{+2}$ levels are found to be less than 1 μg. per mg. of wet tissue.

The results of the animal study are presented in Table I.

TABLE I

| Rat No. | DEGREE OF CALCIFICATION | | |
|---|---|---|---|
| | X-Ray[2] | Extraction[1] | Histology[3] |
| SDHP - Treated Porcine Cusp Tissue | | | |
| 1 | 0/6 | 0.25 ± 0.02 | 0/1* |
| 2 | 0/6 | 0.26 ± 0.03 | 0/2 |
| 3 | 0/6 | 0.27 ± 0.03 | 0/2 |
| 4 | 0/6 | 0.28 ± 0.02 | 0/2 |
| 5 | 0/6 | 0.28 ± 0.03 | 0/1* |
| Controls: Non-SDHP-Treated Porcine Cusp Tissue | | | |
| 1 | 4/6 | 4.02 ± 4.81 | 2/2 |
| 2 | 4/6 | 8.07 ± 6.48 | 2/2 |
| 3 | 3/6 | 4.22 ± 7.19 | 2/2 |
| 4 | 3/6 | 2.29 ± 3.3 | 2/2 |
| 5 | 2/6 | 2.51 ± 2.15 | 1/1* |

[1]Average of 4 values, μg $Ca^{++}$/mg wet wt. tissue
[2]Evaluated by visual examination; 4/6 = 4 of 6 samples evidenced a significant degree of calcification.
[3]Evaluated by visual examination of stained samples; 2/2 = 2 samples evidenced a significant degree of calcification.
*Second sample was not recovered Three control samples of abdominal muscle tissue were taken from each of the rats at the same time the abdominal muscle containing the implanted SDHP-treated and non-SDHP-treated porcine cusp tissue samples was excised from the sacrificed animals. These control samples were taken from a location in the muscle away from the site of the implanted porcine cusp tissue. The $Ca^{+2}$ levels in the abdominal muscle control samples were determined by the atomic absorption spectrophotometric method described above. The $Ca^{+2}$ level in the abdominal muscle control samples is indicative of the amount of $Ca^{+2}$ which one would expect to find in the implanted porcine cusp tissue as a result of its exposure to the host's normal physiological processes and without the occurrence of any mineralization.

The average $Ca^{+2}$ level in the abdominal muscle control samples of the rats in whose abdominal muscle the SDHP-treated porcine cusp tissue had been implanted was 0.08±0.07 micrograms per milligram (μg. per mg.) of wet tissue (overall average of 3 determinations on each of 5 rats). The average $Ca^{+2}$ level in the explanted SDHP-treated porcine cusp tissue which has been implanted in the abdominal muscle was 0.27±0.02 μg. per mg. wet tissue (overall average of 4 determinations on each of 5 rats). It was concluded from this data that no mineralization had occurred in the SDHP-treated cusp tissue. This conclusion is consistent with and supported by the X-ray and histology results set forth under the heading "SDHP-Treated Porcine Cusp Tissue" in Table I.

The average $Ca^2$ level in the abdominal muscle control samples taken from the control rats (i.e., those rats in whose abdominal muscle the non-SDHP-treated porcine cusp tissue had been implanted) was 0.48±0.13 μg. per mg. wet tissue (overall average of 3 determinations on each of 5 rats). The average $Ca^{+2}$ level in the explanted non-SDHP-treated porcine cusp tissue which had been implanted in the abdominal muscle of the control rats was 4.22±5.04 μg. per mg. wet tissue. It was concluded from this data that a significant degree of mineralization had occurred in the non-SDHP-treated cusp tissue. This conclusion is consistent with and supported by the X-ray and histology results set forth under the heading "Controls: Non-SDHP-Treated Porcine Cusp Tissue" in Table I.

As illustrated by the data in Table I, the SDHP treatment was effective to substantially inhibit calcification of the porcine valve cusp tissue for a period of 12 weeks under the severe calcification conditions inherent in the rat test. The correlation between calcification in the rat test and human experience is such that the extensive calcification detected in the rat control group after 12 weeks would not be expected to occur in humans until after several years exposure. The SDHP treatment would accordingly be expected to retard calcification in humans for an additional period of years beyond that normally experienced prior to the onset of calcification.

The procedure described above is one that has produced good results and constitutes a preferred embodiment of the present invention. The scope of the present invention, however, is not to be limited by the details of the described procedure, and it will be apparent to those skilled in the art that many variations in this procedure are possible. For example, the concentration of the SDHP treatment solution may range from about 0.1 to 5.0% or higher, and other water soluble phosphate esters or salts of phosphate esters may be substituted for the SDHP. Treatment temperatures may range from about 5° C. to 50° C.; and treatment times may vary from as little as 1 day to as much as 4 weeks.

The pH of the treatment solution may range from about 2.0 to about 10.0 and will depend on the chemical structure of the water soluble phosphate ester and the presence of desired buffering agents as well as the composition of the aqueous electrolyte solution if such is used instead of distilled water in preparing the phosphate ester treatment solution. In addition, other ingredients both active and inactive may be utilized in combination with the phosphate ester in the treatment solution. Such variations may be developed by those skilled in the art with little or no experimentation to suit individual desires.

While the preceding example has also been limited to the treatment of porcine heart valve cusp tissue, the invention is equally applicable to the treatment of veins, arteries, and other tissues taken from pigs, other animals, or humans, all of which are known to be useful for implantation in humans. Human umbilical cords, for example, have been used as arterial grafts after fixation in glutaraldehyde. Similarly, porcine and bovine arteries and veins have also been suggested for use as arterial grafts and A-V fistula grafts. All such tissues are suitable for use in the practice of the present invention.

We claim:

1. A method for inhibiting the mineralization of fixed natural tissue after implantation in a living body comprising contacting fixed natural tissue intended for implantation with an aqueous solution of a water soluble phosphate ester having the formula

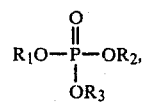

wherein at least one of $R_1$, $R_2$ and $R_3$ is an alkyl group having from 7 to 15 carbon atoms.

2. The method of claim 1 wherein the pH of the aqueous solution ranges from about 2 to about 10.

3. The method of claim 1 wherein said phosphate ester is a monoalkyl ester and said alkyl group is selected from the group consisting of decyl, dodecyl and myristyl.

4. The method of claim 1 wherein the alkyl group is a straight chain aliphatic group.

5. The method of claim 1 wherein the alkyl group is a branched aliphatic group.

6. The method of claim 1 wherein $R_1$ is an alkyl group having from 7 to 15 carbons, $R_2$ is hydrogen, and $R_3$ is selected from the group consisting of sodium, potassium, ammonium and organic amine.

7. The method of claim 6 wherein said alkyl group is selected from the group consisting of decyl, dodecyl and myristyl.

8. The method of claim 6 wherein said alkyl group is a dodecyl group.

9. The method of claim 1 wherein said natural tissue is contacted with said solution for a time sufficient to effectively inhibit future calcification of said tissue after implant.

10. The method of claim 1 wherein said natural tissue is contacted with said solution for a period of at least 24 hours at ambient temperature.

11. The method of claim 1 wherein the concentration of said phosphate ester in said solution is from about 0.1 to 5% by weight.

12. The method of claim 11 wherein the solution has a pH of from about 2 to about 10.

13. The method of claim 11 wherein said solution comprises, in addition to said phosphate ester, up to about 1% by weight of sodium chloride, up to about 0.05% by weight each of potassium chloride, magnesium sulfate heptahydrate and dipotassium hydrogen phosphate, and up to about 0.1% by weight of sodium dihydrogen phosphate.

14. The method of claim 11 wherein said solution comprises, in addition to said phosphate ester, about 0.8% by weight of sodium chloride, about 0.04% by weight of potassium chloride, about 0.02% by weight each of magnesium sulfate heptahydrate and dipotassium hydrogen phosphate, and about 0.08% by weight of sodium dihydrogen phosphate.

15. The method of claim 14 wherein the pH of said solution is about 3.

16. A method for inhibiting the calcification of fixed natural tissue after implantation in a living body which comprises contacting fixed tissue intended for implantation with a solution comprising sodium dodecyl hydrogen phosphate for a time sufficient to effectively inhibit future calcification of said tissue after implantation.

17. The method of claim 16 wherein said solution comprises from about 0.1 to 5% by weight sodium dodecyl hydrogen phosphate.

18. The method of claim 16 wherein said tissue is contacted with said solution for a time of at least about 7 days.

19. The method of claim 16 wherein the pH of said solution ranges from about 2 to about 10.

20. The method of claim 19 wherein the concentration of sodium dodecyl hydrogen phosphate is about 1%.

21. The method of claim 19 wherein the tissue is contacted with said solution of sodium dodecyl hydrogen phosphate for a period of about 7 days at ambient temperature.

22. The method of claim 16 wherein said solution includes, in addition to sodium dodecyl hydrogen phosphate, up to about 1% by weight of sodium chloride, up to about 0.05% by weight each of potassium chloride, magnesium sulfate heptahydrate and dipotassium hydrogen phosphate, and up to about 0.1% by weight of sodium dihydrogen phosphate.

23. The method of claim 16 wherein said solution includes, in addition to sodium dodecyl hydrogen phosphate, about 0.8% by weight sodium chloride, about 0.04% potassium chloride, about 0.02% by weight each of magnesium sulfate heptahydrate and dipotassium hydrogen phosphate, and about 0.08% by weight of sodium dihydrogen phosphate.

24. The method of claim 23 wherein the pH of said solution is about 3.

25. The method of claim 16 wherein the fixed tissue is a glutaraldehyde-fixed porcine heart valve.

26. The method of claim 16 wherein said living body is a human.

* * * * *